(12) United States Patent
Martin et al.

(10) Patent No.: US 12,329,387 B2
(45) Date of Patent: Jun. 17, 2025

(54) ADJUSTABLE LENGTH MEDICAL DEVICES

(71) Applicant: Maduro Discovery, LLC, Campbell, CA (US)

(72) Inventors: Brian B. Martin, Santa Cruz, CA (US); Jason Miller, Los Gatos, CA (US)

(73) Assignee: Maduro Discovery, LLC, Los Gatos, CA (US)

( * ) Notice: Subject to any disclaimer, the term of this patent is extended or adjusted under 35 U.S.C. 154(b) by 0 days.

(21) Appl. No.: 18/585,739

(22) Filed: Feb. 23, 2024

(65) Prior Publication Data
US 2024/0285281 A1 Aug. 29, 2024

Related U.S. Application Data

(60) Provisional application No. 63/486,524, filed on Feb. 23, 2023.

(51) Int. Cl.
*A61M 39/10* (2006.01)
*A61B 17/12* (2006.01)

(52) U.S. Cl.
CPC ....... *A61B 17/12109* (2013.01); *A61M 39/10* (2013.01); *A61B 2017/1205* (2013.01)

(58) Field of Classification Search
CPC ...... A61B 17/12109; A61B 2017/1205; A61B 2017/3443; A61M 39/10; A61M 39/1011; A61M 2039/1066; A61M 25/0905; F16L 37/138; Y10T 403/459

See application file for complete search history.

(56) References Cited

U.S. PATENT DOCUMENTS

| | | | |
|---|---|---|---|
| 5,109,867 A * | 5/1992 | Twyford, Jr. ..... | A61M 25/0905 600/585 |
| 5,282,478 A * | 2/1994 | Fleischhaker, Jr. ......... | A61M 25/0905 600/585 |
| 5,507,731 A | 4/1996 | Hernandez et al. | |
| 5,637,102 A * | 6/1997 | Tolkoff ................. | F16L 33/225 604/536 |
| 5,882,344 A * | 3/1999 | Stouder, Jr. ........ | A61B 17/3417 604/164.11 |
| 6,508,807 B1 * | 1/2003 | Peters ................ | A61M 39/1011 604/905 |
| 2006/0006649 A1 | 1/2006 | Galdonik et al. | |
| 2008/0051676 A1 | 2/2008 | Melsheimer | |
| 2021/0338975 A1 | 11/2021 | Cottone | |
| 2022/0354359 A1 * | 11/2022 | Dreyfuss .............. | A61B 1/3132 |

FOREIGN PATENT DOCUMENTS

WO WO 2024/178353 8/2024

* cited by examiner

*Primary Examiner* — Diane D Yabut

(74) *Attorney, Agent, or Firm* — Levine Bagade Han LLP

(57) ABSTRACT

Medical devices that are adjustable in length while a portion of the device remains positioned within the body and methods of use.

21 Claims, 14 Drawing Sheets

ADJUSTABLE LENGTH MEDICAL DEVICES

CROSS-REFERENCE TO RELATED APPLICATIONS

This application is a non-provisional of U.S. Provisional Application No. 63/486,524 filed Feb. 23, 2023, the entirety of which is incorporated by reference.

FIELD OF THE INVENTION

Medical devices that are adjustable in length while a portion of the device remains positioned within the body and methods of use.

BACKGROUND OF THE INVENTION

Medical procedures that require navigation of a guide catheter from an externa vascular incision through the vasculature to access a target site at a region of interest that is spaced or remote from that external vascular incision site involve many challenges. In some cases, the medical caregiver uses the catheter itself to perform the procedure. Alternatively, the caregiver inserts another intermediate catheter into a previously placed guide catheter to perform a procedure at or near the region of interest. In either case, the advancement of any catheter requires the medical practitioner to select a catheter with a length that is sufficient to reach the target site. In those cases where one or more intermediate catheters are used, the practitioner must consider lengths for both catheters to not only ensure that the catheters can reach the target site but also to ensure that the intermediate catheter can advance from the distal end of the guide catheter to reach the treatment site. FIG. 1A illustrates an example of a guide catheter 20 inserted into a radial artery of a patient 2 where a distal end 24 of the guide catheter is positioned through a tortuous vascular path to a target site 10 with an intermediate catheter 30 inserted within the guide catheter 20. FIG. 1B illustrates an example of a guide catheter 20 and intermediate catheter 30 inserted into a femoral artery 14 of the patient 2 and advanced through a tortuous vascular path into a target site 10.

When driving any catheter from outside of the body where the catheter extends through an external incision and into vasculature, the medical caregiver can spend a significant amount of time navigating the catheter through the tortuous vascular paths to the region of interest. The act of navigating the catheter directly against a vessel wall creates additional risks to the patient, such as causing unintentional damage to the vessel walls or dislodging plaque or other calcifications from the vessel wall that can potentially cause a stroke if the particles migrate further into the vasculature and obstruct blood flow. Therefore, any time a medical caregiver must replace a guide catheter with another guide catheter of a different size or the same size but a different length, not only is the duration of the procedure increased but the patient also is again exposed to the risks described above. Replacement of the intermediate catheter may not involve the same risks as replacement of a guide catheter, but navigation of a replacement intermediate catheter will still increase the procedure time. Apart from the risks to the patient, the medical facility must maintain a supply of catheters of various lengths, and there is increasing procedure cost each time a catheter is used and discarded for another catheter.

There remains a need to provide a medical caregiver with the ability to adjust a length of a catheter, or other medical devices, while the device remains positioned within the anatomy.

SUMMARY OF THE INVENTION

The devices of the present invention allow for adjustable length devices, such as catheters (which include a variety of tubular devices as described below). In one variation, the present disclosure includes adjustable medical devices. For example, such an adjustable medical device can include a first tubular member having a first proximal end and a first distal end; a second tubular member having a second proximal end and a second distal end; a first connector affixed to the first proximal end and a second connector affixed to the second distal end, where the first connector and the second connector each have a plurality of splines and a plurality of slots, where both the plurality of splines and the plurality of slots extend helically along an axial direction to a free end of each of the first connector and the second connector, and where each spline in the plurality of splines is spaced apart from an adjacent spline by a slot from the plurality of slots; and wherein in a partially joined configuration, the plurality of splines and the plurality of slots from the first connector nest respectively with the plurality of slots and the plurality of splines from the second connector, and where relative rotation in a first direction between the first connector and the second connector allows for engaging the first connector and the second connector in a fully joined configuration, and where relative rotation in a second direction allows for uncoupling of the first connector and the second connector.

In an additional variation, an adjustable medical device can further include a sleeve member positioned over the first connector and the second connector, such that in the fully joined configuration, the sleeve member covers the plurality of slots and the plurality of splines on both the first connector and the second connector to increase resistance to relative rotation between the first connector and the second connector, where the sleeve member is removable from the plurality of slots and the plurality of splines to permit decoupling of the first connector and the second connector. The sleeve member can be positioned over the first connector and the second connector in any number of ways, e.g., sliding, evertable, wrapped, etc. In some variations, the sleeve member is configured to compress the first connector and the second connector.

The adjustable medical devices described herein can include a hub located at the second distal end.

In an additional variation, the adjustable medical devices can further include a third tubular member having a third connector affixed to a third distal end of the third tubular member, the third connector having a plurality of splines and a plurality of slots that are configured to nest with the plurality of slots and the plurality of splines of the first connector when the second connector is decoupled from the first connector, where a length of the third tubular member is different than a length of the second tubular member.

The splines described herein can include an end that comprises a tapered shape or narrowed shape to allow for ease of nesting within the respective slot. In addition, the slots can also comprise a mating tapered shape to receive the tapered shape for ease of connecting.

Variations of the devices include devices having an angle of the plurality of splines relative to an axis of the first connector is 45 degrees or greater. However, any angle is within the scope of this disclosure.

Additional variations of the adjustable medical device can include a flow occluding device having at least one flow occluding element, wherein the flow occluding device is advanceable through the second distal end such that the at least one flow occluding element is positioned within the first tubular member distal to the first connector. The flow occluding device can also optionally include an alignment structure that extends from the first connector when decoupled from the second connector.

In another variation, this disclosure includes a medical component, for use with a second device having a second connector, the medical component comprising: a first tubular member having a first proximal end and a first distal end; a first connector affixed to the first proximal end having a plurality of splines and a plurality of slots, where both the plurality of splines and the plurality of slots extend helically along an axial direction to a free end of the first connector, and where each spline in the plurality of splines is spaced apart from an adjacent spline by a slot from the plurality of slots; and wherein the plurality of splines are configured to nest with the second connector and the plurality of slots are configured to receive a portion of the second connector through relative rotation in a first direction between the first connector and the second connector, where relative rotation in a second direction allows for uncoupling of the first connector and the second connector.

In another variation, the disclosure includes a catheter configured for coupling to a catheter extension having a mating connector, the catheter comprising: a tubular member having a proximal end and a distal end; a connector affixed to the proximal end and having a plurality of splines and a plurality of slots, where both the plurality of slots and the plurality of splines extend helically along an axial length to a free end of each of the connector, and where each spline is spaced apart from an adjacent spline by a slot from the plurality of slots, wherein the plurality of splines can be inserted into the mating connector for coupling the medical catheter to the catheter extension.

Another variation of a device includes a catheter extension configured to couple to a catheter having a mating connector, the catheter comprising: a tubular member having a proximal end and a distal end; a hub affixed to the proximal end; and a connector affixed to the distal end and having a plurality of splines and a plurality of slots, where both the plurality of slots and the plurality of splines extend helically along an axial length to a free end of the connector, and where each spline is spaced apart from an adjacent spline by a slot from the plurality of slots, wherein the plurality of splines can be inserted into the mating connector for coupling the catheter extension to the catheter.

The disclosure also includes methods for accessing a body lumen in a patient. For example, one variation of such a method includes advancing a distal portion of a first tubular segment of a catheter to a target location within the body lumen, where a proximal portion of the first tubular segment remains exterior to the body, and where the proximal portion comprises a first connector coupled to a second connector of a second tubular segment, where the first connector and the second connector each include a plurality of splines nested together to form a connector assembly; removing a sleeve member from a portion of the connector assembly; rotating the first connector and the second connector relative to each other to detach the plurality of splines causing the first connector and the second connector to decouple, where the distal portion of the first tubular segment remains within the body lumen; joining a third tubular segment having a third connector that includes a plurality of splines to the first connector by rotating the third connector and the first connector relative to each other such that the plurality of splines on the first connector and the plurality of splines on the third connector nest together causing first connector and the second connector to form a second connector assembly; and securing the second connector assembly to prevent relative rotation between the first connector and the third connector.

Variations of the method include removing the sleeve member by everting the sleeve member from the portion of the connector assembly; sliding the sleeve member from the portion of the connector assembly; and unwrapping the sleeve member from the portion of the connector assembly. In additional variations, a sleeve member can comprise a slit that permits positioning of the sleeve member over the connector assembly without having to slide the sleeve member along the connector assembly.

Variations of the method can further include positioning an occlusion device having an occlusion element from the second tubular segment into the first tubular segment such that the occlusion element is positioned distally to the first connector to block blood flow.

Another variation of a method for accessing a body lumen in a patient can include advancing a distal portion of a first segment of a catheter to a target location within the body lumen, where a proximal portion of the first segment remains exterior to the body, and where the proximal portion comprises a first connector coupled to a second connector of a second tubular segment having a hub; and, while the distal portion first tubular segment remains within the body lumen, decoupling the first connector and the second connector by opposite relative rotation of the first connector to the second connector, such that the second tubular segment and the hub separate from the first segment.

Another method of the present disclosure involves a method for preparing for a medical procedure. For example, such a method can include providing a medical device tubing having a connector assembly securing a first distal segment of the medical device to a second proximal segment, where the second proximal segment includes a hub located at a proximal end and where the connector assembly includes a first connector coupled to a second connector, where the first connector is affixed to a proximal end of the first distal segment and the second connector is affixed to a distal end of the second tubular segment; and decoupling the first connector and the second connector by oppositely relative rotation of the first connector to the second connector, such that the second tubular segment and the hub are removed from the medical device tubing.

It is understood that the features and aspects of the methods, devices, and other systems described herein can be combined with other methods, devices, and other systems.

DETAILED DESCRIPTION

The catheter configuration discussed herein can be used in a variety of devices where it is desirable to have the ability to change a length of the device while it remains positioned within the body. The configurations described herein can be incorporated into various medical devices. The use of the term catheter or catheters includes but is not limited to, distal access catheters, sheaths, introducers, guide catheters, balloon catheters, intracranial support catheters, micro catheters, arterial line catheters, central venous catheters, pulmonary artery catheters, coronary and cardiac catheters, and peripheral catheters, medical tubing, and/or any device having a tubular portion that is used to deliver a working end, substances, or other devices to a site within the anatomy. Furthermore, the construction features of the improved connector are not limited to in-dwelling medical devices and can be used for any device requiring tubing.

Figure 1A:
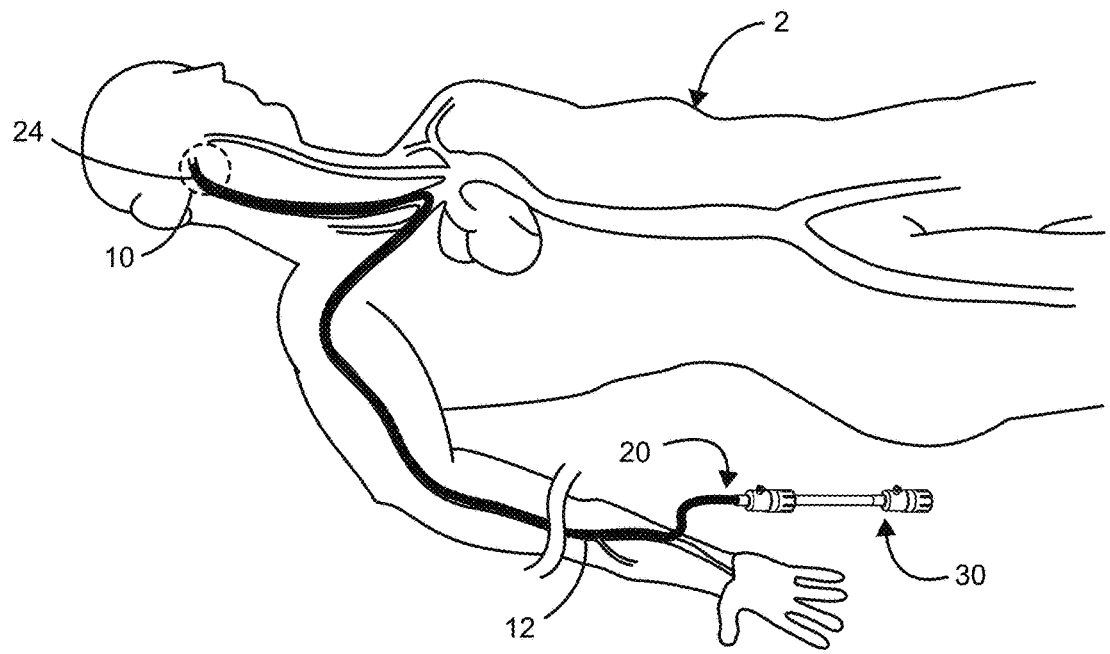
FIGS. 1A and 1B illustrate examples of a guide catheter inserted into a radial artery or a femoral artery of a patient.
Figure 1B:
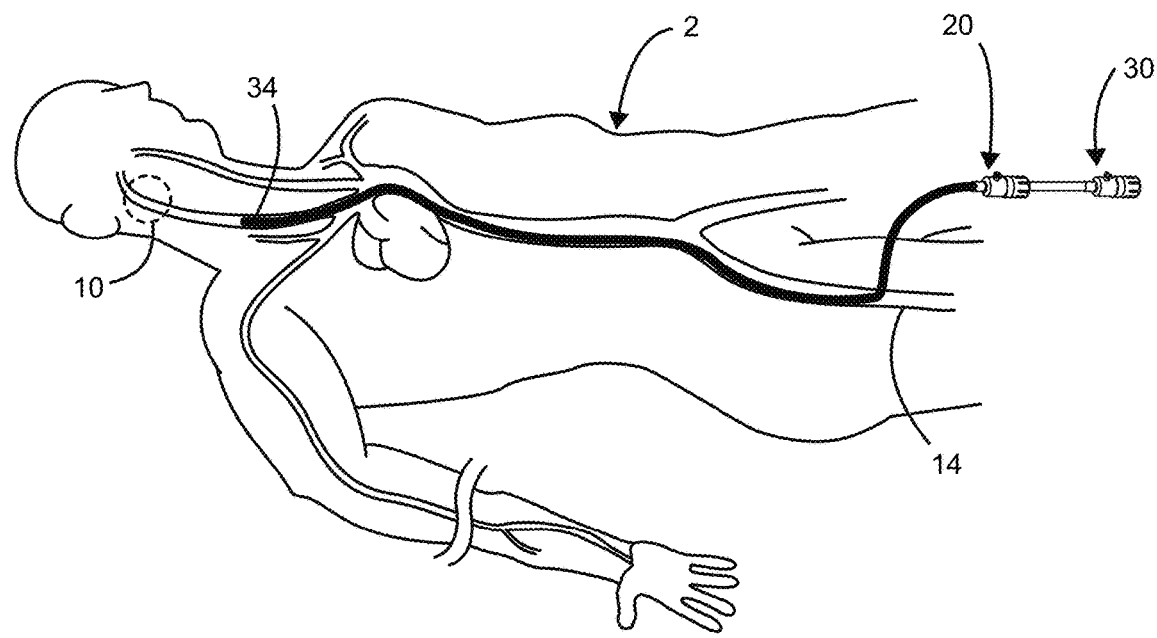
Figure 2A:
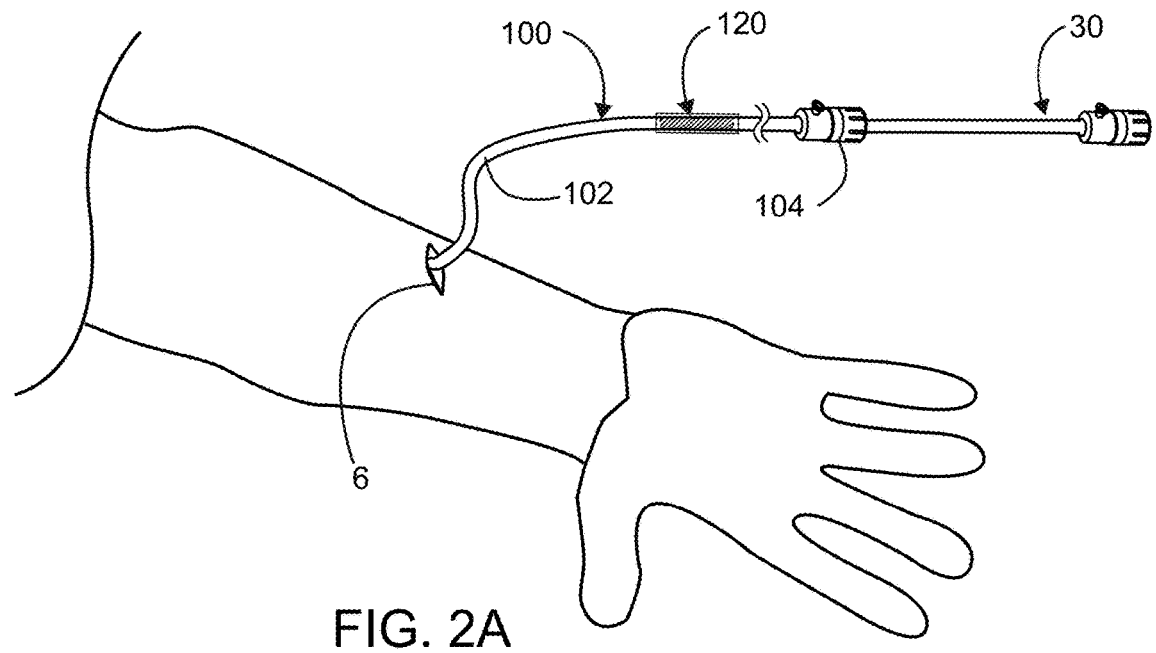
FIG. 2A illustrates a variation of an improved device that allows for customized adjustment of a length of the device while the device remains implanted within the vasculature.
Figure 2B:
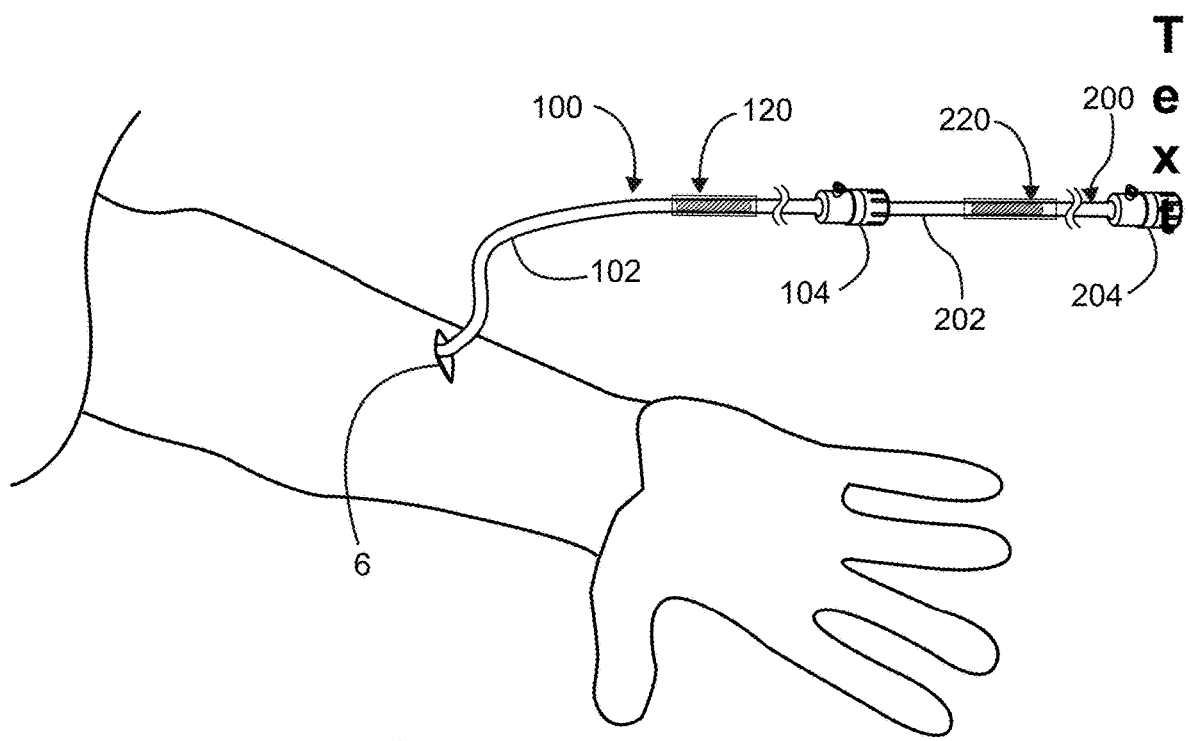
FIG. 2B shows an intermediate device that includes its own connector assembly positioned within an exterior device having its own connector assembly.

FIG. 2A illustrates a variation of an improved device 100, which, in this variation, comprises a guide catheter having an improved connector assembly 120 that allows for customized adjustment of a length of the tubing 102 of the device 100 while the device remains implanted within the vasculature. FIG. 2A illustrates the device 100 as being inserted into a radial artery via an incision 6 with a secondary or intermediate catheter 30 extending through a hub 104 of the device 100. It is noted that FIG. 2A illustrates the device 100 inserted into the radial artery via the incision 6 for purposes of illustration only. In practice, devices having connector assemblies as described herein can be positioned in the body through any vascular or other body passage. FIG. 2B illustrates a second variation in which a device 100 is positioned similar to the device shown in FIG. 2A, however, FIG. 2B shows an intermediate device 200 that includes its own connector assembly 220. As noted below, in the variation of FIG. 2A, the intermediate catheter 30 is removed to decouple the connector assembly 120. The variation of FIG. 2B, which includes a connector assembly 220 on the tubing 202 of the device that permits detaching the hub 204 such that the tubing 202 remains in place. Accordingly, the hub 104 of the device 100 can be removed over the tubing 202 upon decoupling of the connector assembly 120 of the exterior/guide catheter 100.

Figure 3:
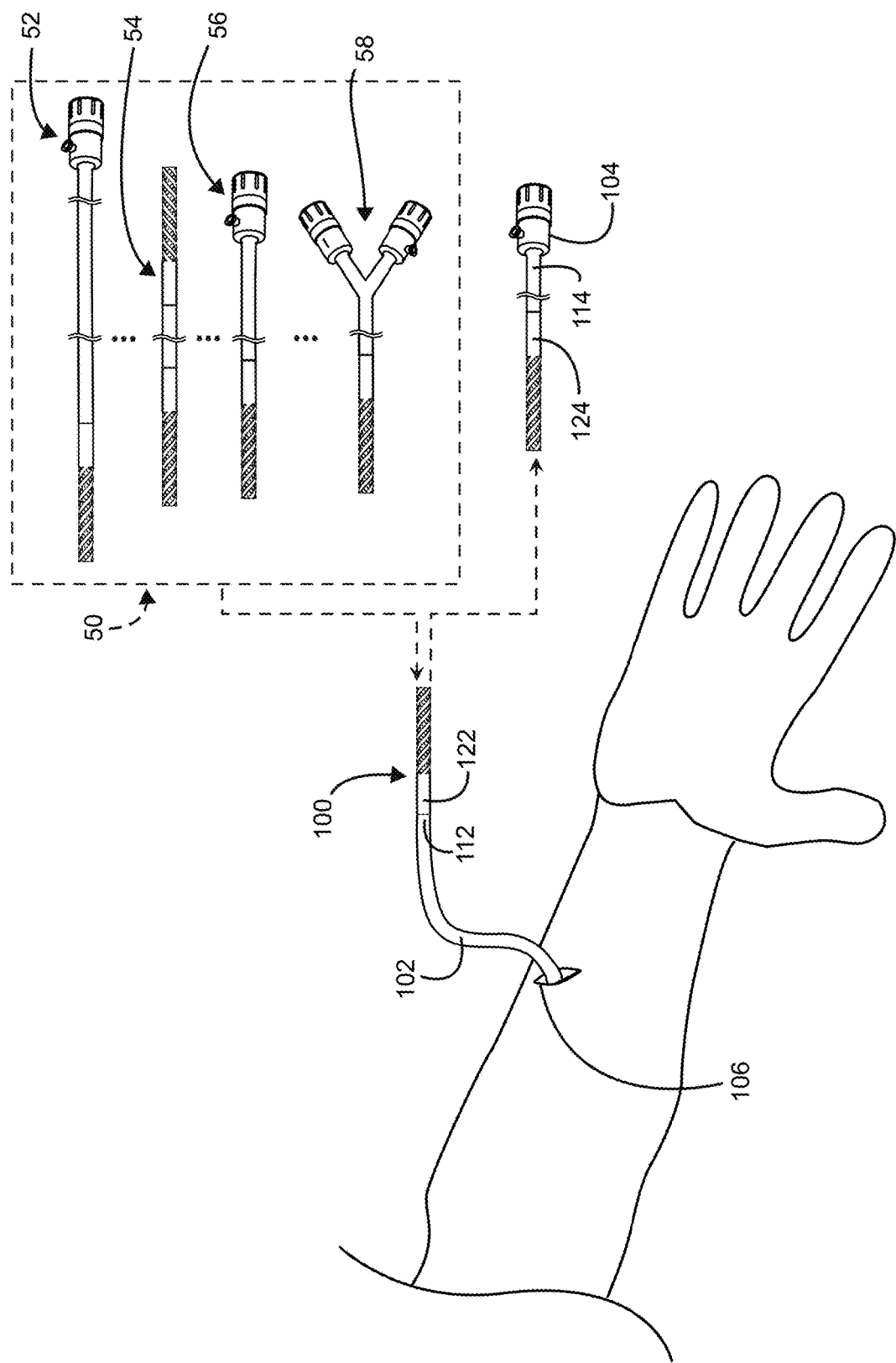
FIG. 3 illustrates the interchangeability of the devices described herein.

FIG. 3 illustrates a concept of the interchangeability of the devices described herein. As shown, a device 100 like that shown in FIG. 2A remains implanted within the incision site 6 such that a tubing 102 of the device 100 is not removed from the body. In this variation the intermediary device/catheter (30 in FIG. 2A) is removed from the guide catheter 100. However, as noted above with regard to FIG. 2B, an intermediary device (e.g., 200 in FIG. 2B) designed for decoupling can remain within the body. The connector assembly (120 shown in FIGS. 2A and 2B) is decoupled to separate a first connector 122 that remains affixed to a proximal end 112 of the tubing 102 (for convenience the implanted tubing is referred to as the first tubing). The second connector 122 and attached second tubing 114 are separated from the implanted device 100. Various means of separating the coupling and arresting blood flow are discussed below.

Once the first connector 122 and second connector 124 are decoupled, a medical caregiver can select any one of a variety of catheter/extension components from an inventory 50. The inventory 50 illustrated in FIG. 3 is non-exhaustive and simply shows a sample number of devices, including but not limited to: a long extension 52 and a shorter extension 56, that can be coupled to the first connector 122 (where the lengths are relative to the original second connector 124, second tubing 114, and hub 104. The inventory 50 can also include an extension 54 that has connectors on both ends, which allows further customization of the indwelling device 100. While not illustrated, the inventory 50 can include extensions where the hubs are different so as to provide the caregiver with different connector options for the device 100. Moreover, while the extensions 52, 54, 56 shown in the inventory comprise single tubes, alternate variations can include extensions with two or more tubes joining to a single connector 58, which would allow for a single line catheter device to be converted to a multi-connector catheter device while the tubing 102 remains positioned within a body of the patient.

Figure 4A:
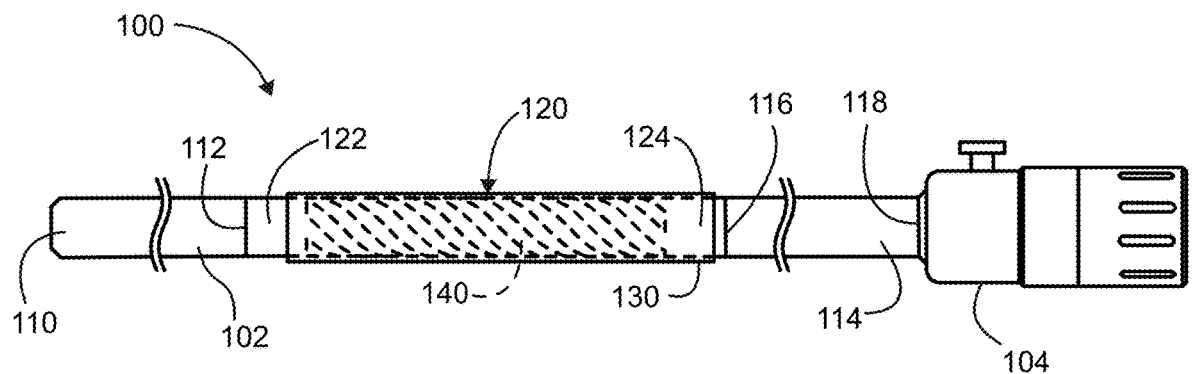
FIGS. 4A and 4B illustrate respective side and perspective views of an adjustable medical device.
Figure 4B:
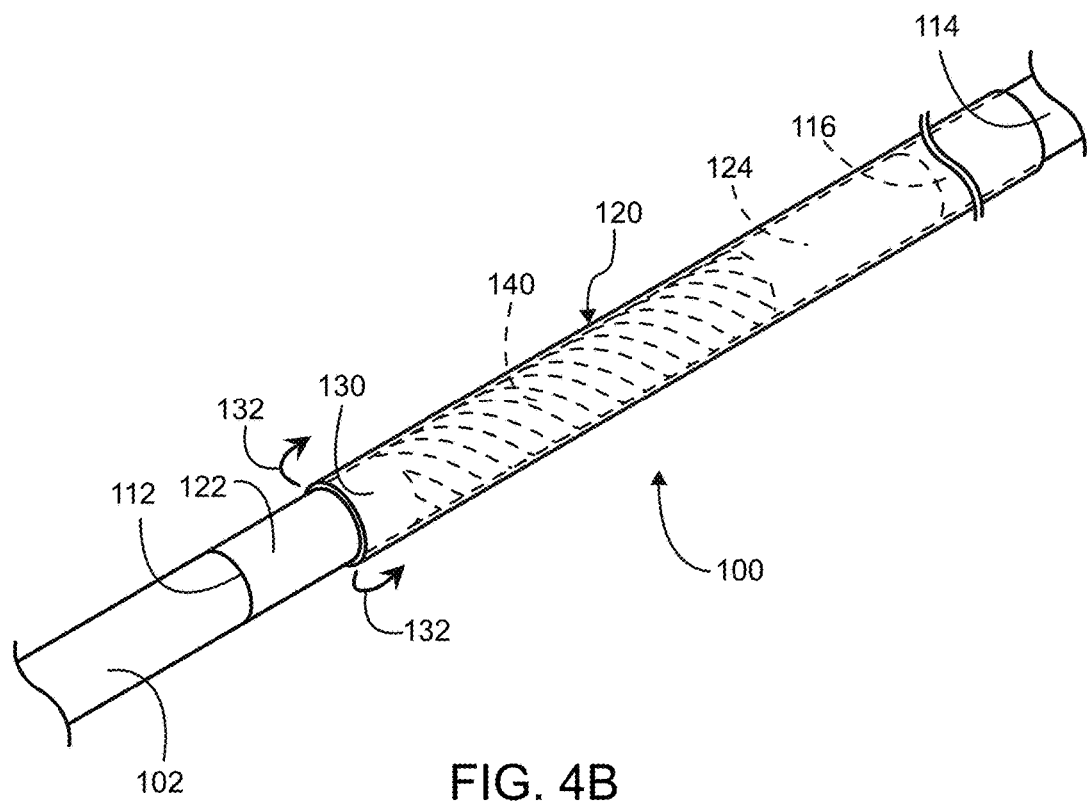

FIGS. 4A and 4B illustrate respective side and perspective views of an adjustable medical device 100 that is similar to those shown in the figures discussed above. As illustrated, the device 100 includes a tubular member 102 having a proximal end 112 with a connector 122 affixed to the tubular member 102. A distal end 110 of the tubular member 102 is intended for insertion into the body lumen or vessel. The connector 122 is coupled to another connector 124, such that when engaged, the connectors form a connector assembly 120. As discussed below, the connectors 122, 124 each have a plurality of interconnected splines in region 140. Where the splines 140 from each connector 122, 124 nest within slots (not illustrated in FIG. 4A) of the other connector. Connector 124 is affixed to another tubular member 114 at a distal end 116 of that tubular member 114, where the proximal end 118 of the tubular member 114 includes one or more hubs 104 as discussed above. FIG. 4A also shows the device 100 including an optional sleeve member 130 that is located over the spline 140 in the connector assembly 120. The sleeve member 130 typically provides torsional/twisting resistance to the connectors 122, 124 to prevent unintentional de-coupling. Alternate versions of the sleeve member 130 can provide a sealing function in the spline region in addition to or in place of the torsional resistance. When used, the sleeve member 130 can extend over the proximal end 112 of the tubular member 102 to the distal end 116 of the other tubular member 114. Alternatively, or in combination, the sleeve can extend over the connectors. The use of the sleeve member 130 is described below.

Figure 4C:
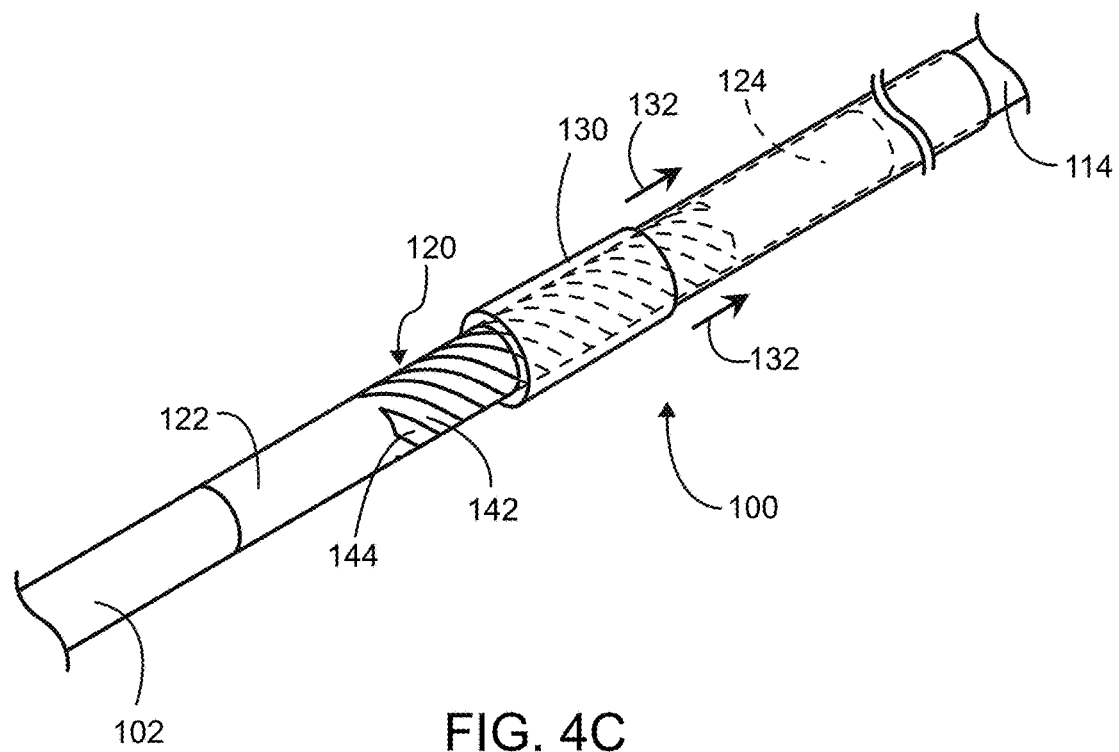
FIGS. 4C and 4D illustrate the connector assembly of device of FIG. 4B with the sleeve member removed from the connector assembly.
Figure 4D:
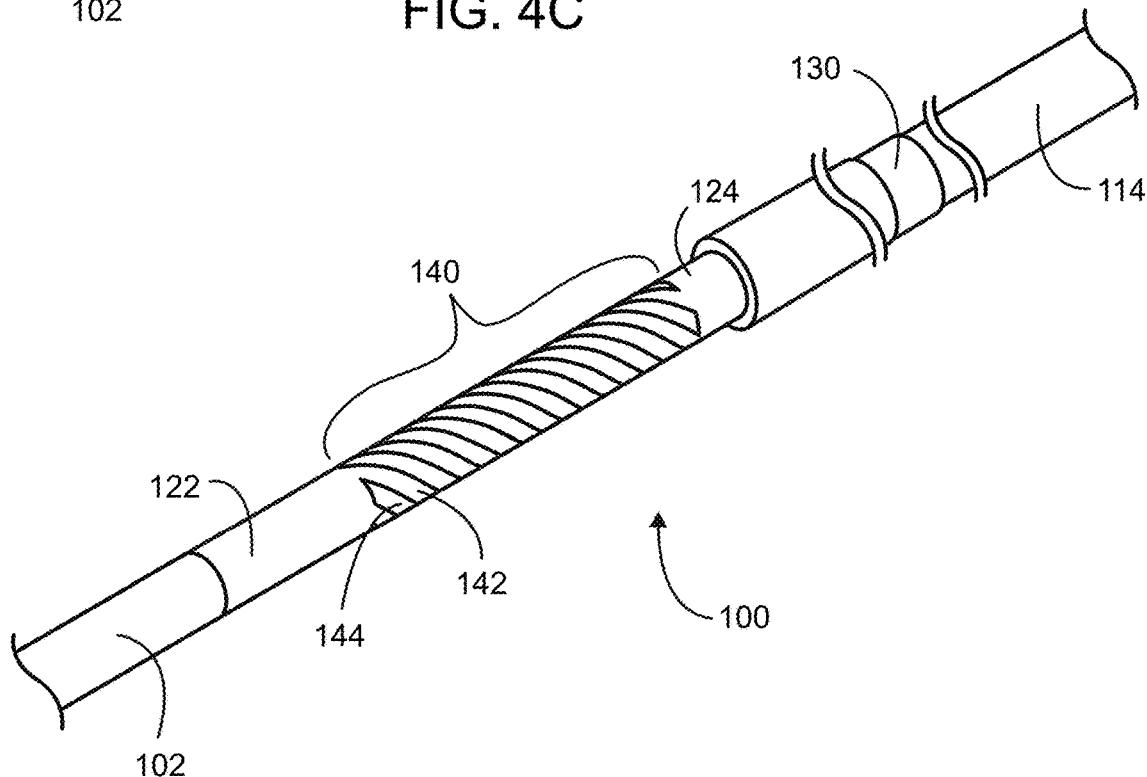

FIGS. 4C and 4D illustrate the connector assembly 120 of device 100 of FIG. 4B with the sleeve member 130 further everted, as shown by arrows 132, to expose the splines 142 of the first connector 122 interconnected with splines 144 of the second connector 124. As shown in FIG. 4D, the sleeve member 130 is positioned such that the spline region 140 is fully uncovered. As noted herein, the figures show the sleeve member 130 being withdrawn over the tubular member 114 that is connected to a hub (104 in FIG. 4A). However, variations of the device 100 include a tubular member that can be withdrawn over the tubing 102 adjacent to the portion of the device that remains within the body/lumen.

Figure 4E:
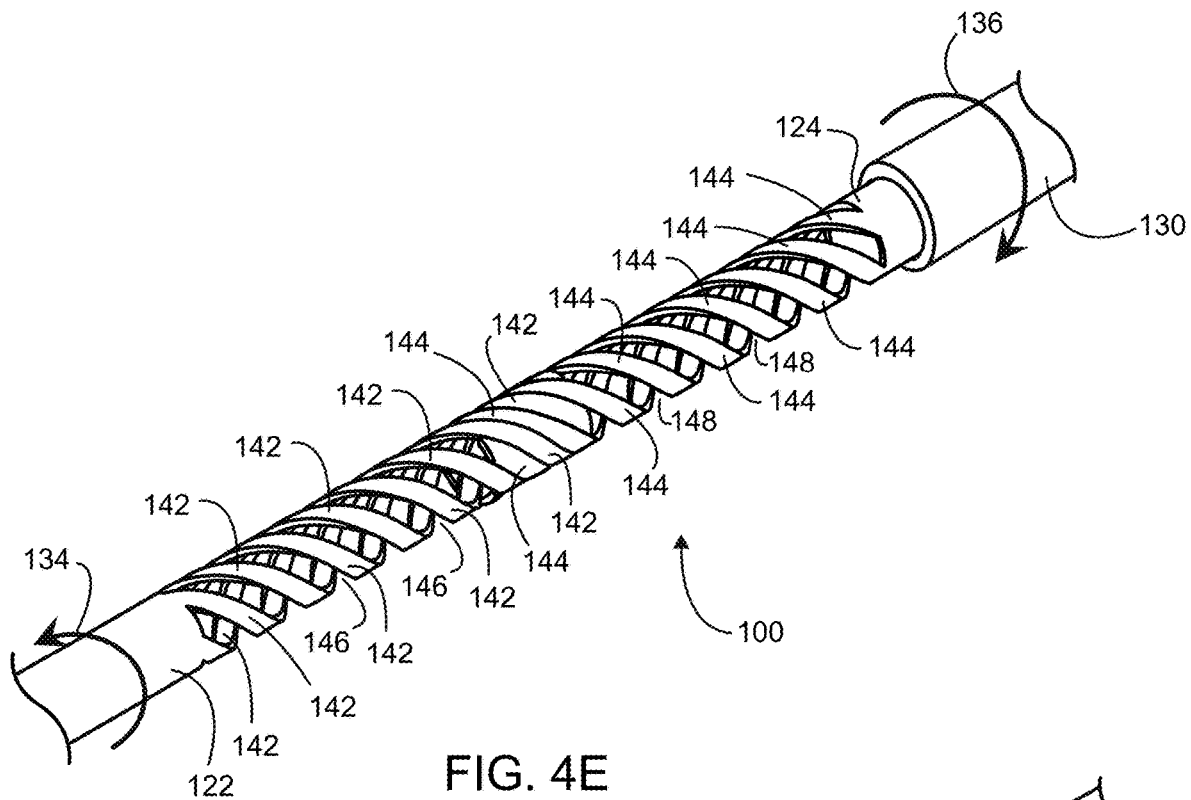
FIGS. 4E and 4F illustrate the connector assembly of the device of FIG. 4B with the sleeve member further everted and the connectors in a partially decoupled and fully decoupled configuration.
Figure 4F:
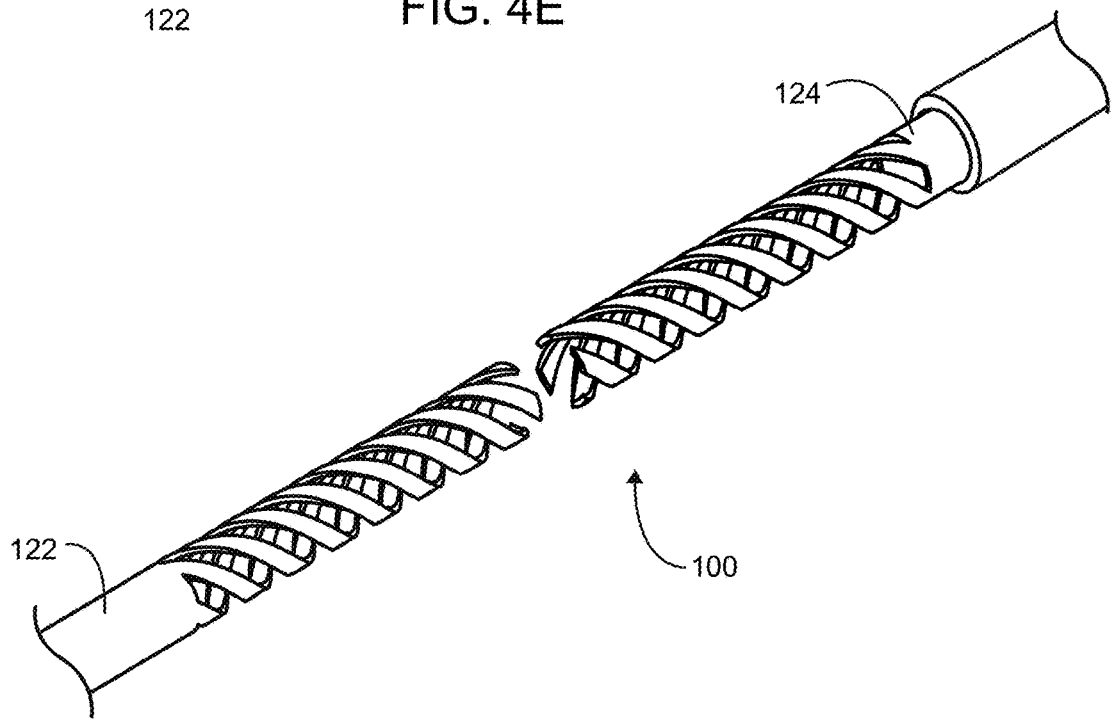

FIGS. 4E and 4F illustrate the connector assembly 120 of device 100 of FIG. 4B with the sleeve member 130 further everted. Either one or both of the joined connectors 122, 124 can be rotated in opposing directions 134, 136 to partially disconnect the connectors 122, 124. It is noted that one or both connectors can be rotated to disengage or engage the connectors. Clearly, relative rotation in an opposing direction between connectors allows for engaging the connectors into a fully joined configuration. FIG. 4F illustrates the connectors 122, 124 when uncoupled. As noted above, the connector remaining in the body (e.g., connector 122) can be coupled to any one of the extensions or devices from an inventory of devices.

Figure 5A:
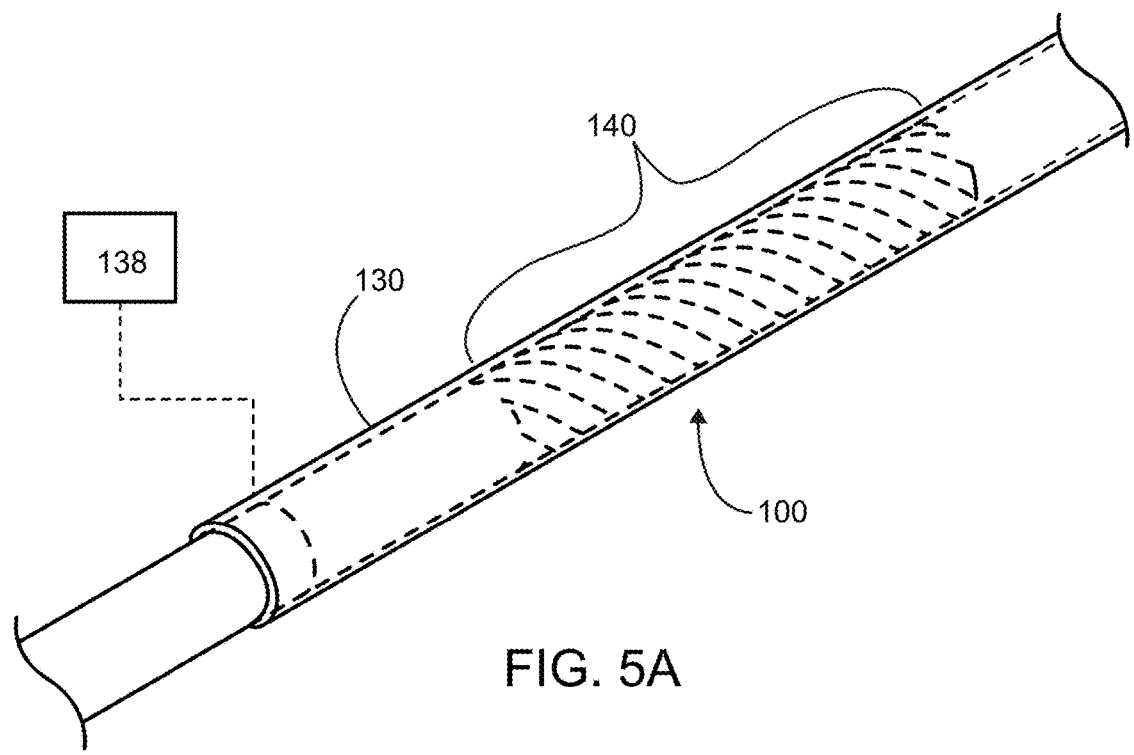
FIGS. 5A and 5B show variations of a device with alternate sleeve members.
Figure 5B:
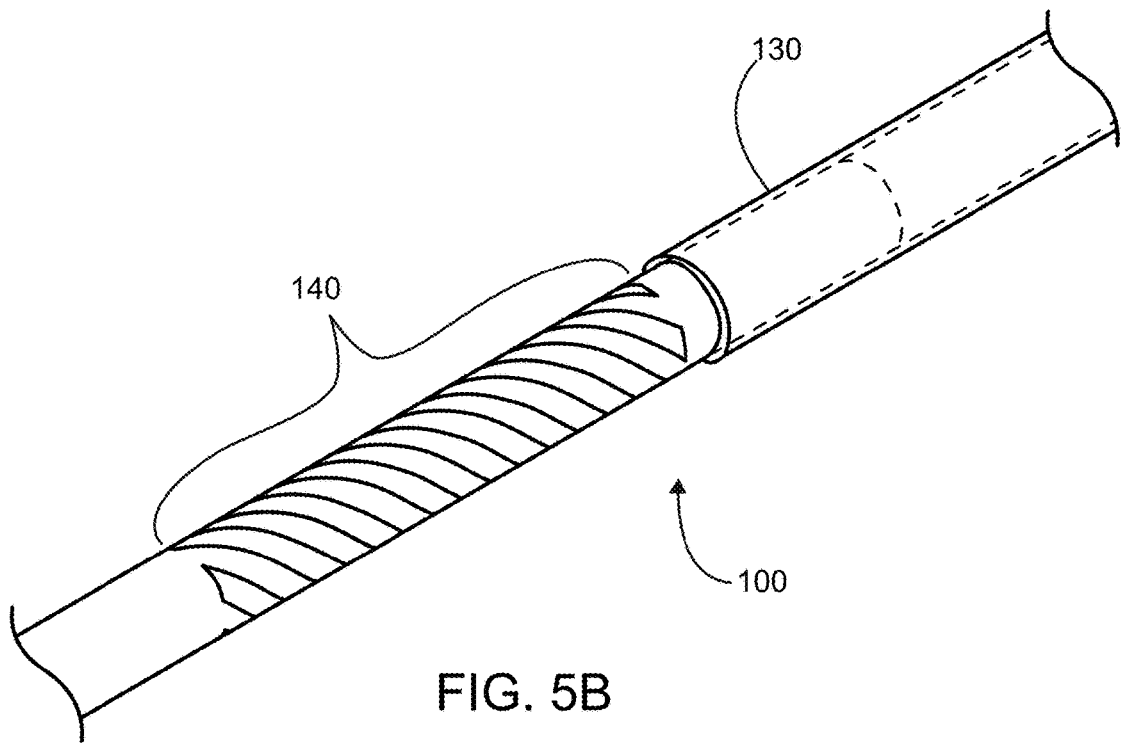

FIGS. 5A and 5B show variations of a device 100 with alternate sleeve members 130. For example, the sleeve member 130 can cover the spline region 140, as shown in FIG. 5A and then slid or translated to uncover the spline region, as shown in FIG. 5B. Alternatively, or in combination, the device 100 can include a fluid, pressure, or electric source 138 that can compress the sleeve 130 about the spline region 140. Compression can also be achieved by simply integrating radially compression mechanical elements into the sleeve. Once uncoupling is required, the source 138 is activated or depressurized to allow easier movement of the sleeve from the fluid, pressure, or electric source 138.

Figure 5C:
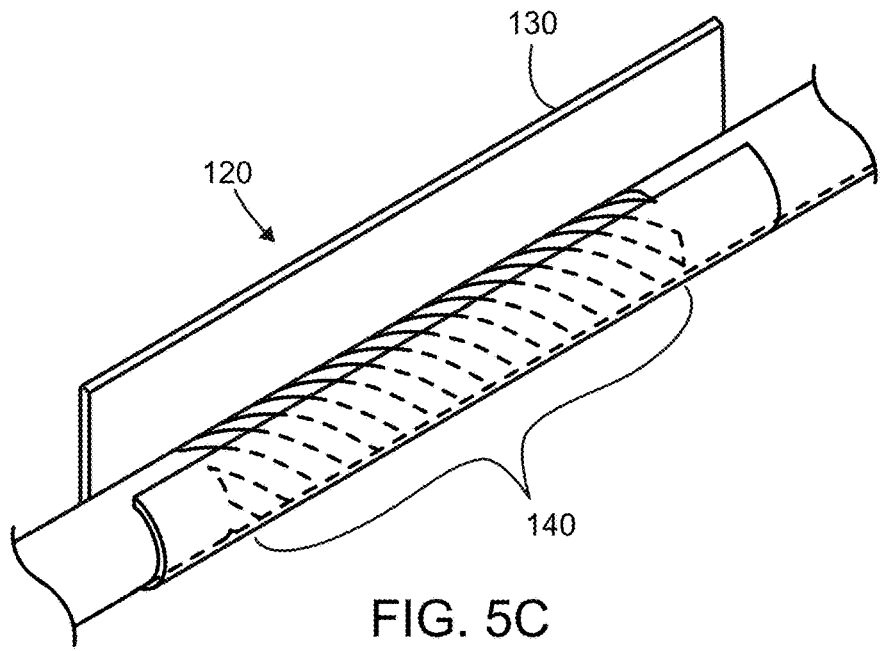
FIG. 5C illustrates another variation of a sleeve member that wraps about the spline region to secure the connector assembly.
Figure 5D:
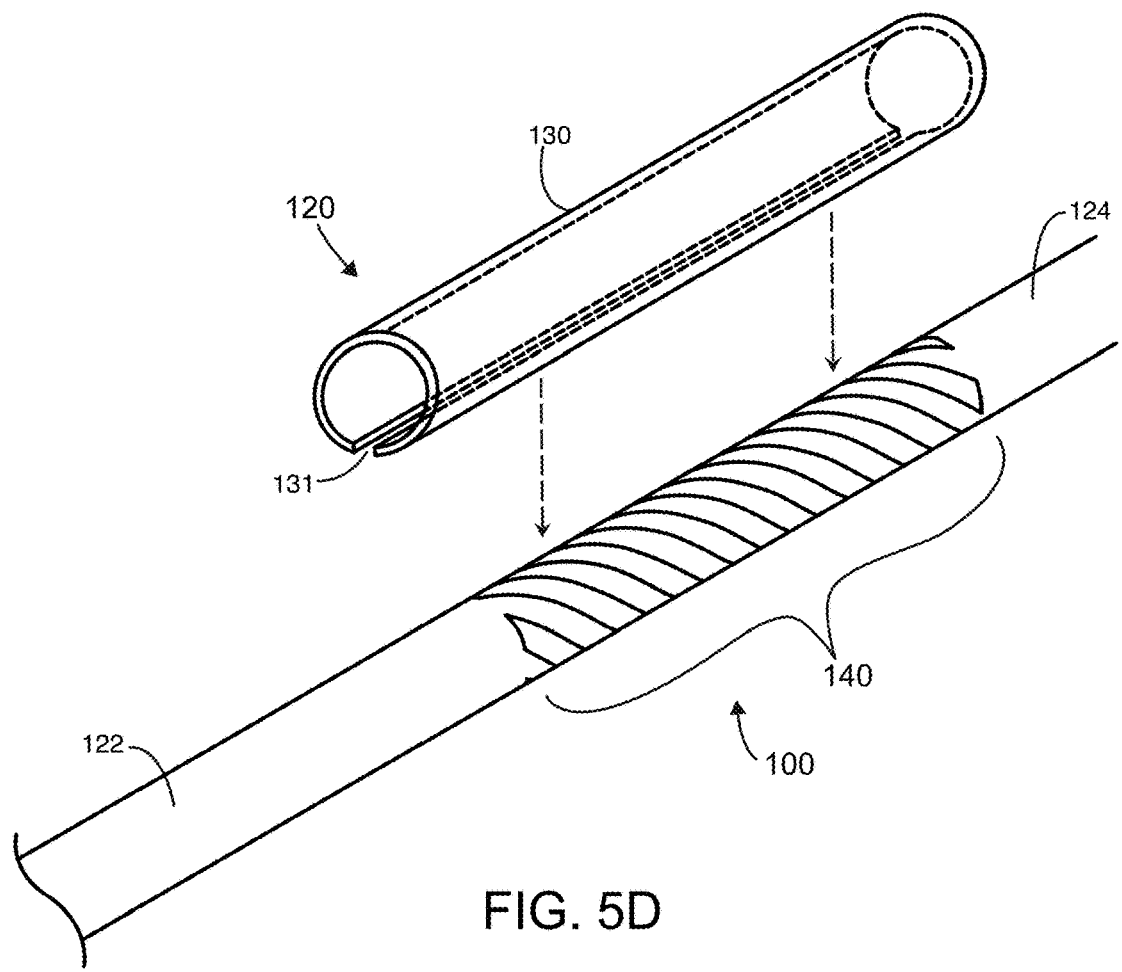
FIG. 5D shows a variation of a sleeve member that is joined in a radial direction over the connector assembly rather than sliding.
Figure 6A:
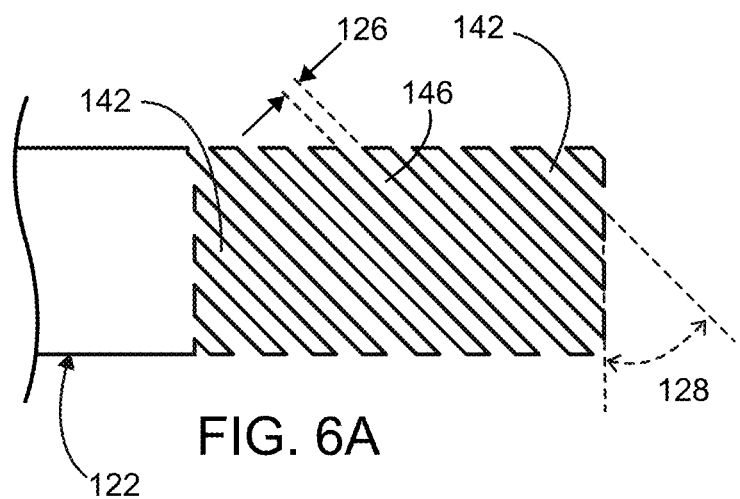
FIG. 6A shows an example of a connector in a flat pattern to illustrate an angle of the splines which can be selected to maintain coupling of the connectors when coupled connectors are pushed, pulled, or encounter opposing axial forces.

FIG. 5C illustrates another variation of a sleeve member 130 that wraps about the spline region 140 to secure the connector assembly 120 and is unwrapped to allow decoupling of the connector assembly. FIG. 5D shows another variation of a sleeve member 130 that has a slit 131 that allows for positioning of the sleeve member 130 over the spline region 140 to secure the connector assembly 120 without the need to slide the sleeve member 130 axially over the connector assembly. In this variation, the portions of the sleeve member 130 adjacent to the slit 131 separate to allow the sleeve member to be positioned coaxially on the spline region 140 to prevent inadvertent rotation of the connectors 122, 124 relative to each other. This connector can also be elastic or malleable. FIG. 6A shows an illustration of a flat pattern view of a connector 122 to illustrate an angle 128 of the splines 142, which can be selected to maintain coupling of the connectors when the device is pushed, pulled, or encounter opposing axial force. While variations of the connectors 122 can include splines having a range of angles 128 (as measured as shown in FIG. 6A). In one variation, the connector can have a 45-degree angle or smaller, which causes the splines to lock together when the connector assembly is pushed together or pulled apart in an axial direction. As noted above, disengagement of the connector assembly requires opposite rotation between the connectors. While the use of a sleeve member (not shown in FIG. 6A) prevents relative rotation between connectors, alternate variations of the device do not require sleeves. For example, the splines 142 (on one or both connectors) can be coated with a polymer or other coating to provide rotational resistance. Also add that polymer or similar coating can be used as a gasket material to help seal the assembly once connected, for maintaining pressure integrity within the catheter shaft. Alternatively, some variations of the device do not require a sleeve or coating. The connectors described herein can be fabricated in any manner known to those skilled in the art. Moreover, the connectors can be a metal alloy, a super elastic material, a polymeric material, or a composite material. FIG. 6A also illustrates a width 126 of the slot 146, which can be adjusted to vary a spacing of the splines 142 and/or a width of the splines 142.

Figure 6B:
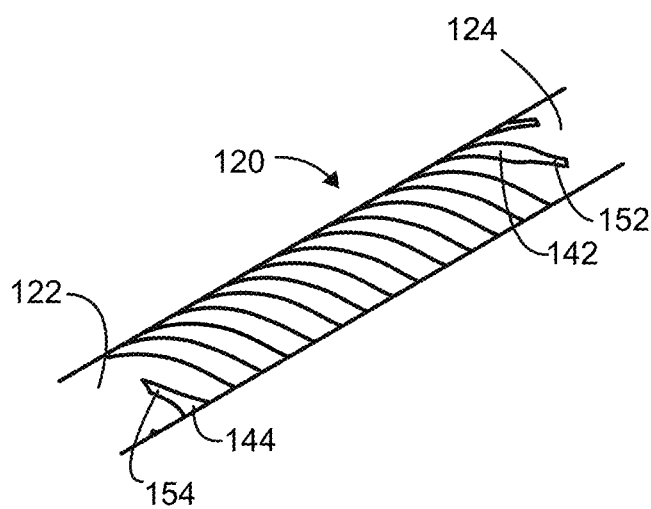
FIG. 6B shows another variation of a connector assembly having features to assist in joining of two connectors.
Figure 6C:
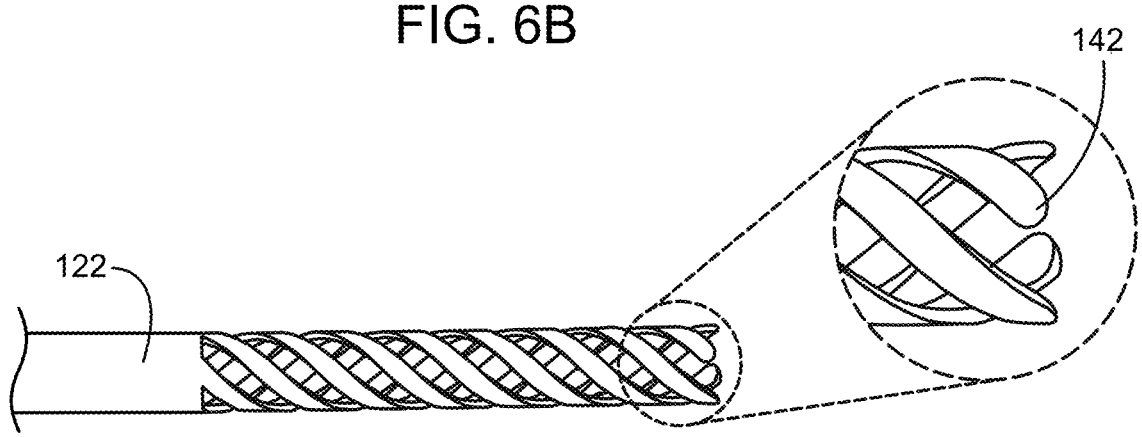
FIG. 6C illustrates a variation where splines are radiused at the ends to help with mating to the opposing connector.

FIG. 6B shows another variation of a connector assembly 120 having features to assist in joining two connectors 122, 124. As shown, the distal end 152 of splines 142 from connector 122 are tapered or sized to ease entry into a corresponding slot when joining the connector 122 to another connector 124. The distal end 154 of the spline 144 of the paired connector 124 can also optionally have a tapered shape. The tapered shape is undersized relative to a width of the slot formed between the splines 142, 144, and the distal end of the slots will be shaped to receive the distal end of the spline. In an additional variation, the slots can be configured to have wider openings at the open end of the connectors, and the splines will have profiles at the respective ends to close against the wider openings of the slots. FIG. 6C illustrates where the splines 142 are radiused at the free ends to help with mating to the opposing connector. In such a variation either one connector 122 can have radiused splines, or both connectors can have radiused splines.

Figure 7A:
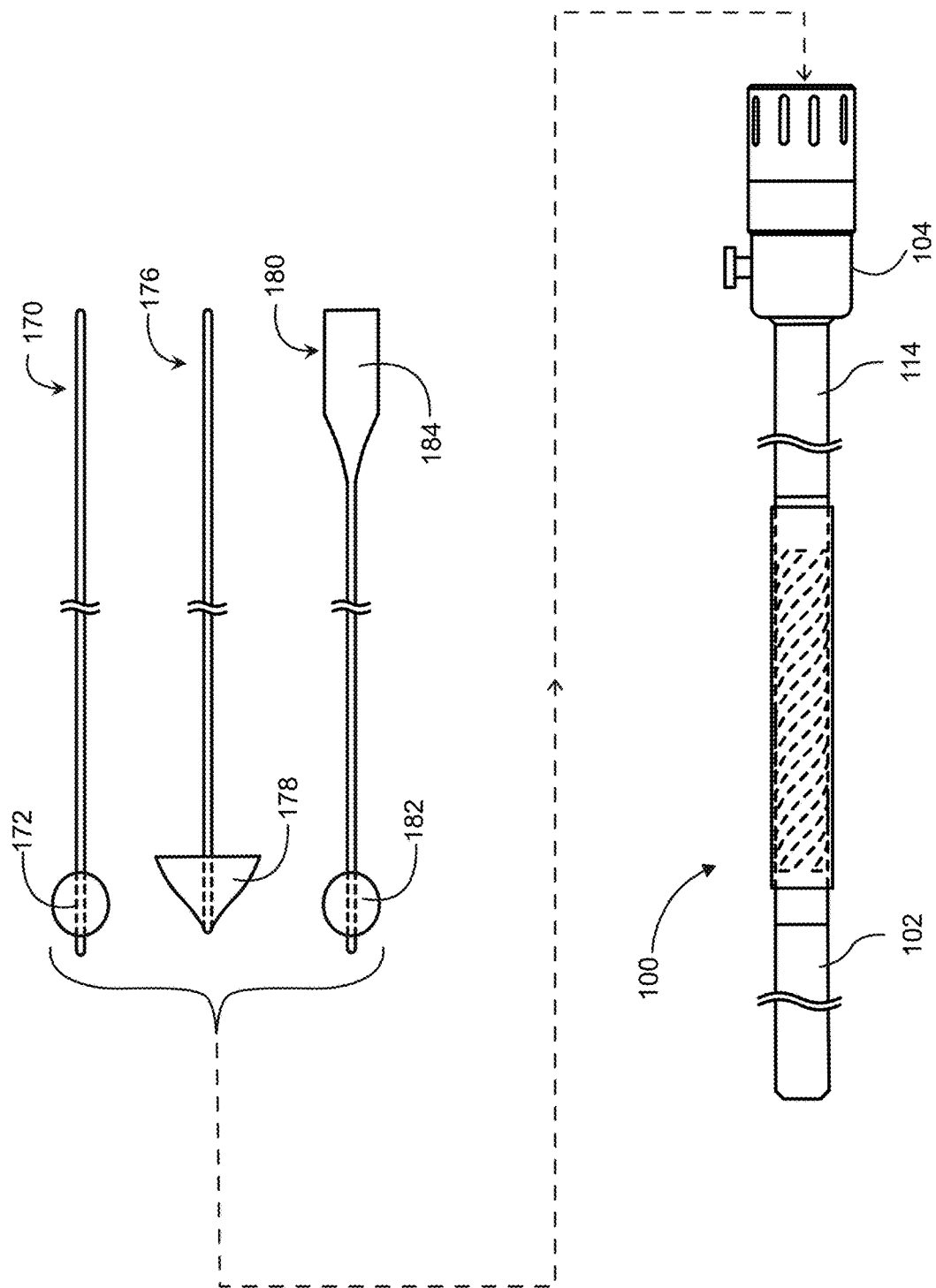
FIG. 7A shows another variation of an adjustable medical device having one or more flow occluding devices.

FIG. 7A shows another variation of an adjustable medical device 100 having one or more flow occluding devices 170, 176, 180. As noted above, a device 100 can be inserted into the vasculature of a patient and allows the medical caregiver to disconnect the hub 104, tubular member, and connector in order to replace these components with a different component selected from an inventory of components 50 (see FIG. 3). However, since the tubular member 102 remains positioned within the vasculature, decoupling the device 100 can result in blood flow through the tubular member 102 and out of the body. Accordingly, the system can include one or more occluding devices 170, 176, 180. Each occluding device 170, 176, 180 can include a balloon or barrier 172, 178, 182 that can self-expand within the passage of the tubular member to occlude without the need for active inflation. Alternatively, the barriers can be actively expanded via a fluid, electrical, or other mechanical means. The occluding devices 170, 176, 180 can also include alignment features 184 that assist in re-coupling connectors.

Figure 7B:
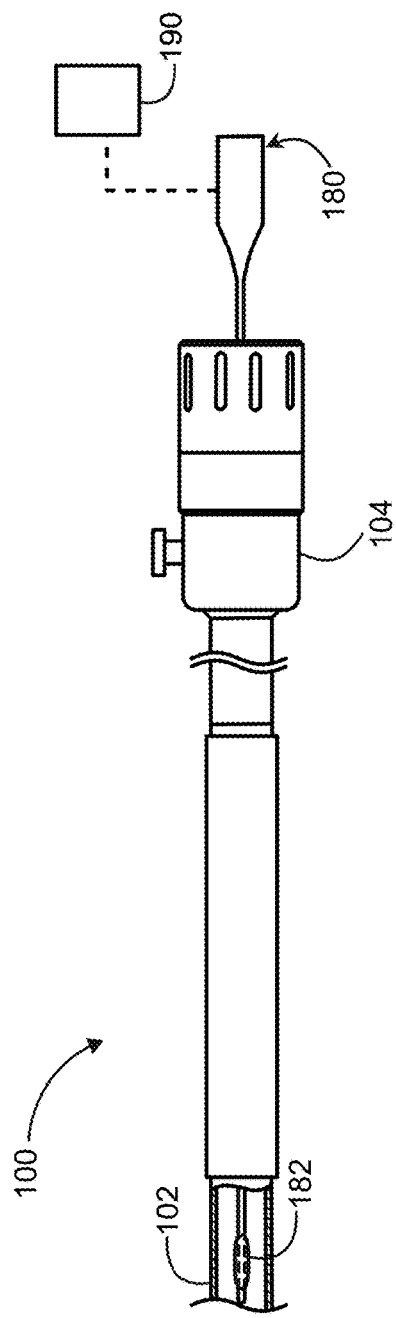
FIG. 7B illustrates the device of FIG. 7A where the occlusion device is advanced within a passage of the tubing in a deflated configuration.
Figure 7C:
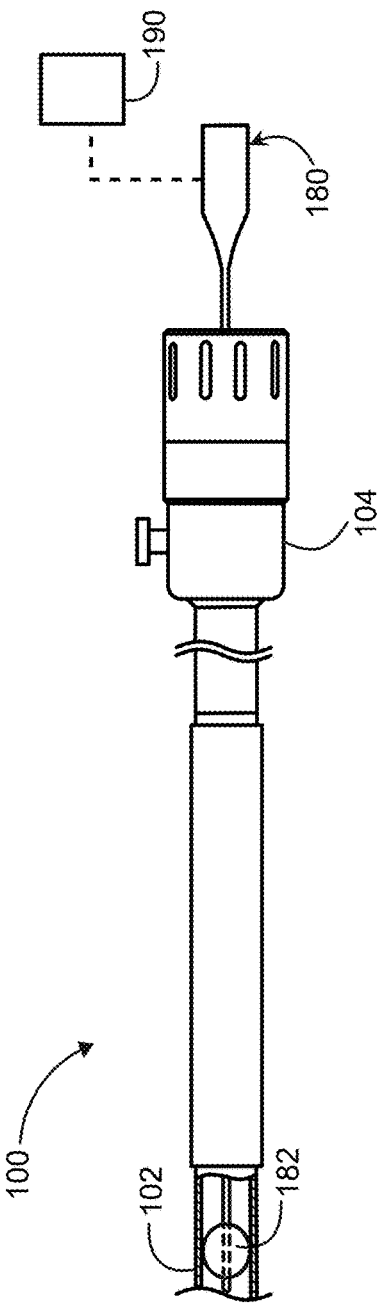
FIG. 7C illustrates the device of FIG. 7B where the occlusion device is inflated within the tubing.

FIG. 7B illustrates the device 100 of FIG. 7A, where the occlusion device 180 is advanced within a passage of the tubing 102. While the occluding component 182 of the occluding device 180 is shown in a deflated configuration, variations of the system can include an occlusion component 182 that does not require inflation. The occlusion device 180 can be coupled to an inflation source or a power source 190. For example, the source 190 can comprise a pump or fluid syringe that simply expands the occlusion component 180. Alternatively, the source 190 can comprise a power source that activates the occlusion component to block the passage of the tubing 102 to prevent blood from flowing proximally in the device 100 as shown in FIG. 7C. The caregiver can now decouple the device 100 without significant blood flow through the tubing because of the occlusion member 182 preventing blood flow out of the device 100.

Figure 7D:
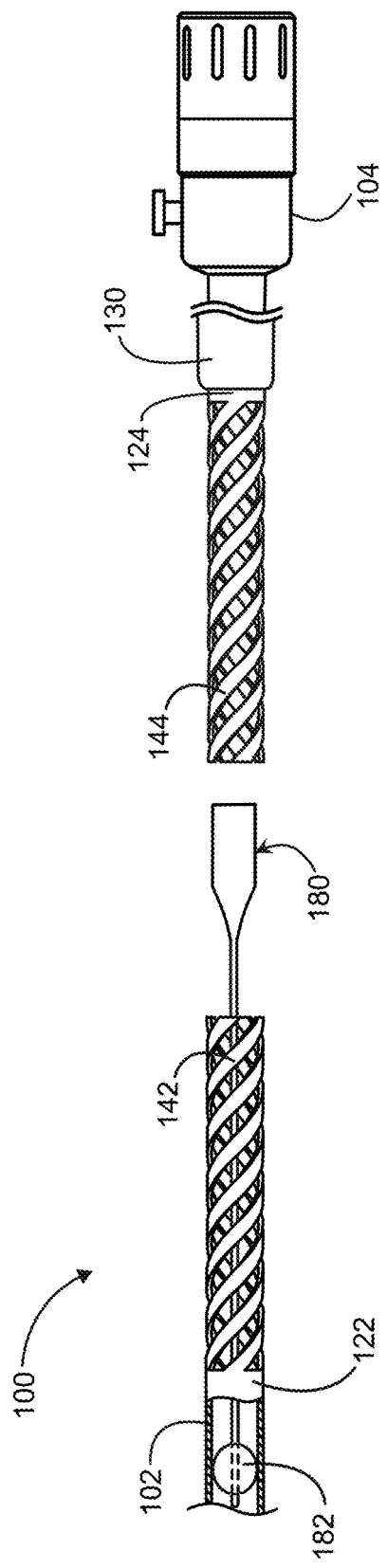
FIG. 7D illustrates the decoupling of connectors while the occlusion device 180 remains positioned within the connector remaining in the body.
Figure 7E:
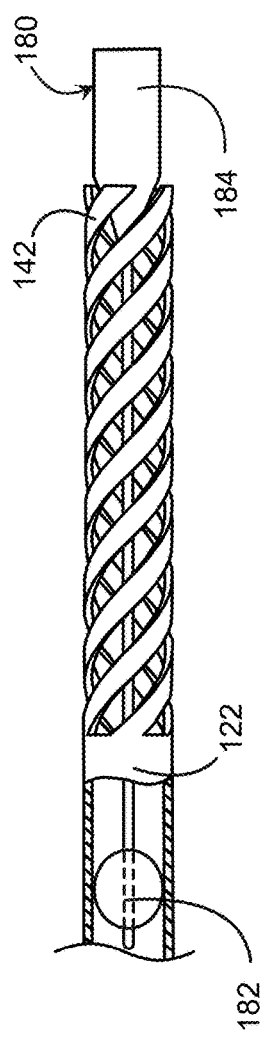
FIG. 7E illustrates the connector of FIG. 7D where an alignment feature from the occluding device is positioned partially (or fully) within the splines of the connector.

FIG. 7D illustrates the decoupling of connectors 122 and 124 when the sleeve member 130 is withdrawn from the connectors 122, 124, allowing connectors 122 and 124 to be rotated relative to one another to decouple splines 142 and 144. As noted above, the sleeve member 130 is optional. As shown, the occlusion device 180 can remain positioned within the connector 122 remaining in the body (e.g., connector 122). FIG. 7E illustrates the connector 122 of FIG. 7D where an alignment feature 184 (e.g., a hub or other tapered surface) is positioned partially (or fully) within the splines 142 of the connector 122, which can aid in alignment of another connector (not shown) to the implanted connector 122. Alternatively, the alignment feature 184 of the occlusion device 180 can remain spaced from connector 122 as shown in FIG. 7D.

Figure 7F:
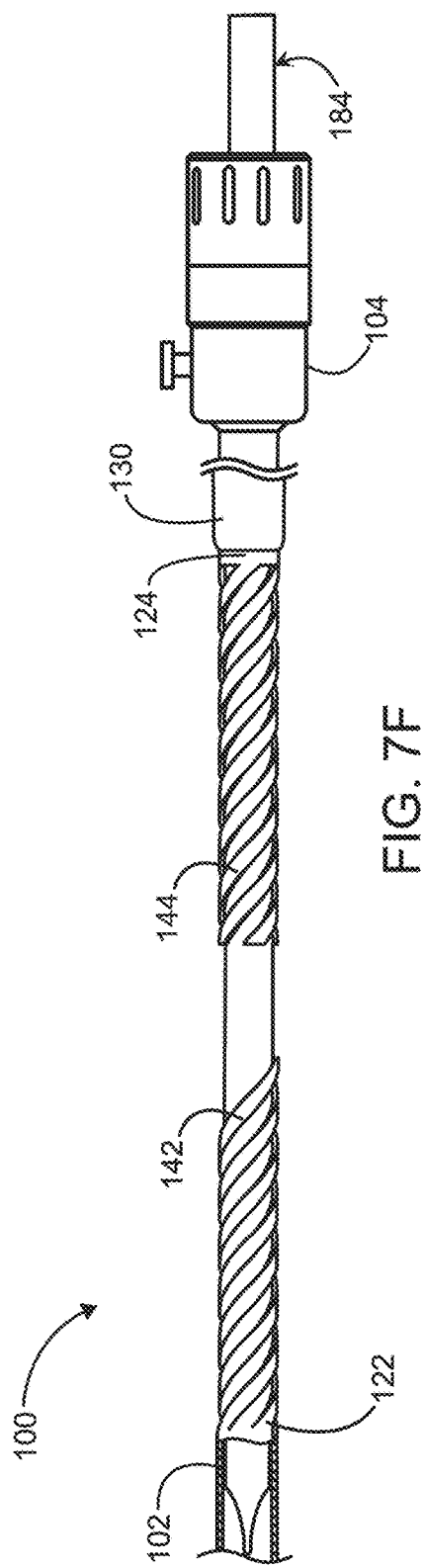
FIG. 7F shows an alignment device that serves both an alignment function and an occluding function by having an occluding portion that is sized in close tolerance to the internal diameter of the connectors to prevent or reduce flow.
Figure 7G:
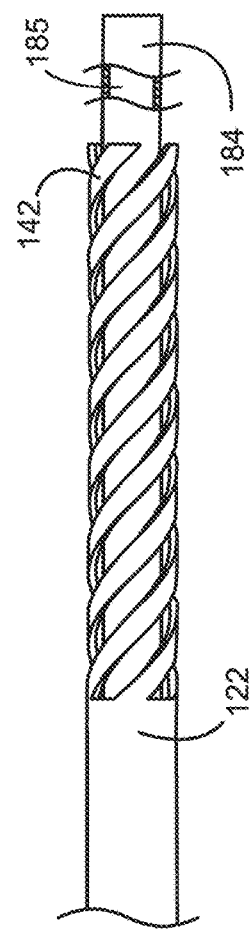
FIG. 7G illustrates a connector having an alignment feature that comprises a tube.
Figure 7H:
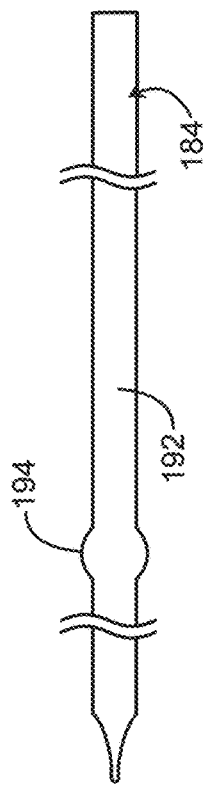
FIG. 7H shows an alignment device similar to that shown in FIG. 7F with a raised surface on the shaft to assist in sealing the connector assembly.

FIG. 7F shows the decoupling of connectors 122 and 124 when the sleeve member 130 is withdrawn from the connectors 122, 124, allowing connectors 122 and 124 to be rotated relative to one another to decouple splines 142 and 144. As noted above, the sleeve member 130 is optional. In this variation, an alignment device 184 serves both an alignment function and an occluding function by having an occluding portion 194 that is sized in close tolerance to the internal diameter of the connectors 122, 124 to prevent or reduce flow. In such a variation, the shaft 192 of the obturator comprises a flow occluding element. FIG. 7G illustrates a connector 122 having an alignment feature 184 that comprises a tube. In this variation, an opposing connector is positioned over the tube 184 such that a clearance between the tube and the splines 142 accommodates a mating connector. The alignment tube 184 includes a lumen 185 to allow flow therethrough. FIG. 7H shows another variation of an alignment device 184 that serves both an alignment function for both connector portions and an occluding function by having a shaft that serves as an occluding portion 192 that is sized in close tolerance to the internal diameter of the connectors 122, 124 to prevent or reduce flow. This variation also includes a region of increased diameter 194 to assist in occluding flow but reduces friction when moving the alignment device 184 from the connector assembly.

Figure 8A:
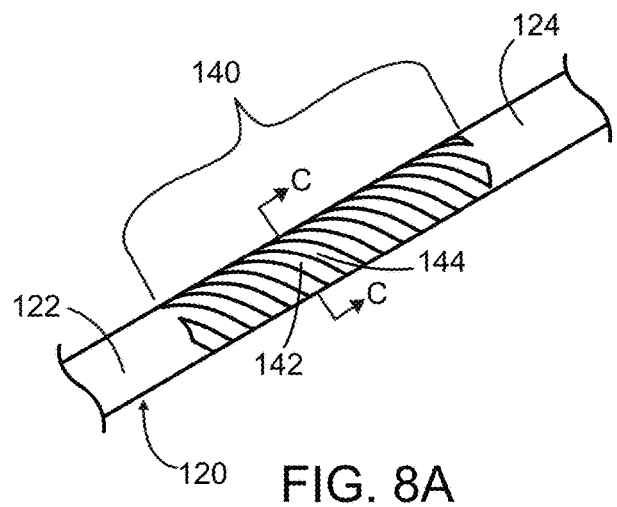
FIG. 8A represents a variation of the splines when connectors are joined together.
Figure 8B:
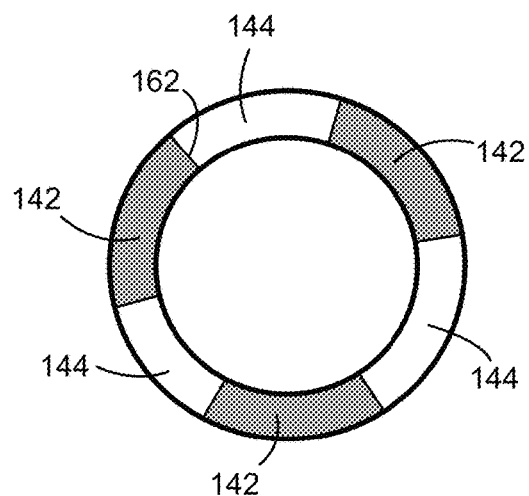
FIGS. 8B to 8D show variations of cross-sections of the connector assembly 120 taken along line C-C from FIG. 8A.
Figure 8C:
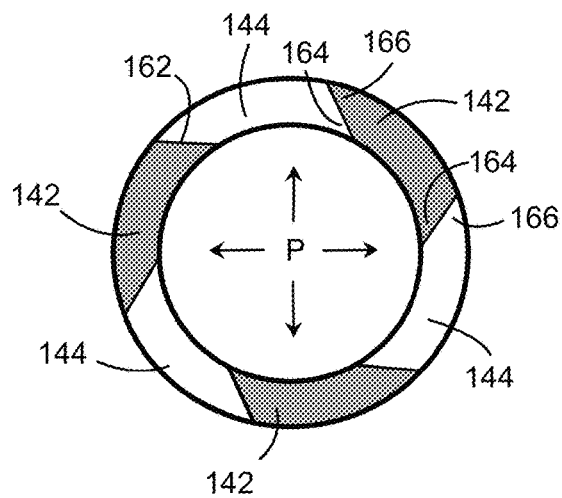
Figure 8D:
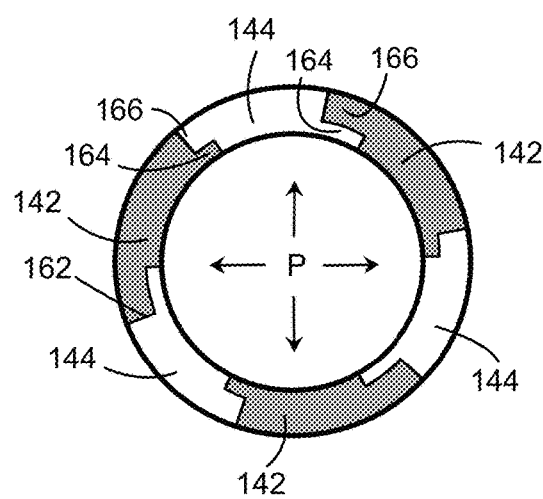

FIG. 8A represents variations of the splines 142, 144 when connectors 122, 124 are joined together. FIGS. 8B to 8D show variations of cross-sections of the connector assembly 120 taken along line C-C from FIG. 8A. FIG. 8B illustrates a variation when spines 142 and 144 have an interface 162 where adjacent edges join. FIG. 8B represents a configuration where each spline 142, 144 comprises a similar cross-sectional area. FIGS. 8C and 8D illustrate additional variations of splines 142, 144 each having inferior side edges 164 and superior edge portions 166 that overlap with adjacent splines at the interface 162 between adjacent splines 142, 144 in a radial direction. FIG. 8C shows an angled interface 162 such that a superior edge 166 of a spline radially overlaps an inferior edge 164 of an adjacent spline. FIG. 8D illustrates a stepped edge 162, where a superior edge 166 of a spline radially overlaps an inferior edge 164 of an adjacent spline. FIGS. 8C and 8D also demonstrate as fluid pressure P increases within the connector assembly, the inferior 164 portion of the edge is forced against the superior edge 166, which increases a fluid seal between adjacent splines 142, 144. As noted above, 162 edges of the splines, or the entirety of the splines, can have a polymer coating that increases the ability of the connector to form a seal between adjacent splines when the connector assembly is pressurized.

As for other details of the present invention, materials and manufacturing techniques may be employed within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

It is important to note that where possible, aspects of the various described embodiments, or the embodiments themselves can be combined. Where such combinations are intended to be within the scope of this disclosure.

The invention claimed is:
1. An adjustable medical device comprising:
 a first tubular member having a first proximal end and a first distal end;
 a second tubular member having a second proximal end and a second distal end;
 a first connector affixed to the first proximal end and a second connector affixed to the second distal end, where the first connector and the second connector each have a plurality of splines and a plurality of slots, where both the plurality of splines and the plurality of slots extend helically along an axial direction to a free end of each of the first connector and the second connector, and where each spline in the plurality of splines is spaced apart from an adjacent spline by a slot from the plurality of slots;

wherein in a partially joined configuration, the plurality of splines and the plurality of slots from the first connector nests respectively with the plurality of slots and the plurality of splines from the second connector such that the plurality of splines of the first connector and of the second connector each alternatingly forms an exterior surface of a joined region of the first connector and the second connector, and where relative rotation in a first direction between the first connector and the second connector allows for engaging the first connector and the second connector in a fully joined configuration, and where relative rotation in a second direction allows for uncoupling of the first connector and the second connector; and wherein the plurality of splines of the first connector radially overlap with the plurality of splines of the second connector such that the plurality of splines each have a superior edge and an inferior edge, where increase of a fluid pressure within the adjustable medical device forces the inferior edge of an adjacent spline against the superior edge to increase a fluid seal between the plurality of splines.

2. The adjustable medical device of claim 1, further comprising a sleeve member positioned over the first connector and the second connector, such that in the fully joined configuration, the sleeve member covers at least a portion of the plurality of slots and the plurality of splines on both the first connector and the second connector to increase resistance to relative rotation between the first connector and the second connector, where the sleeve member is removable from the plurality of slots and the plurality of splines to permit decoupling of the first connector and the second connector.

3. The adjustable medical device of claim 2, where the sleeve member is slidable over the first connector and the second connector.

4. The adjustable medical device of claim 2, where the sleeve member is evertable over the first connector and the second connector.

5. The adjustable medical device of claim 2, where the sleeve member is wrapped over the first connector and the second connector.

6. The adjustable medical device of claim 2, where the sleeve member is configured to compress the first connector and the second connector.

7. The adjustable medical device of claim 1, further comprising a hub located at the second proximal end.

8. The adjustable medical device of claim 1, further comprising a third tubular member having a third connector affixed to a third distal end of the third tubular member, the third connector having a plurality of splines and a plurality of slots that are configured to nest with the plurality of slots and the plurality of splines of the first connector when the second connector is decoupled from the first connector, where a length of the third tubular member is different than a length of the second tubular member.

9. The adjustable medical device of claim 1, wherein an end of at least one of the plurality of splines on the first connector comprises a tapered shape.

10. The adjustable medical device of claim 9, wherein at least one of the plurality of slots of the second connector comprises a mating tapered shape to receive the tapered shape.

11. The adjustable medical device of claim 1, wherein an angle of the plurality of splines relative to an axis of the first connector is 45 degrees or greater.

12. The adjustable medical device of claim 11, further comprising a flow occluding device having at least one flow occluding element, wherein the flow occluding device is advanceable through the second distal end such that the at least one flow occluding element is positioned within the first tubular member distal to the first connector.

13. The adjustable medical device of claim 12, wherein the flow occluding device includes an alignment structure that extends from the first connector when decoupled from the second connector.

14. The adjustable medical device of claim 1, further comprising an alignment device insertable in the first connector and configured to align the second connector to assume the partially joined configuration.

15. The adjustable medical device of claim 14, wherein the alignment device comprises a shaft that is sized to reduce or block fluid flow in the first connector.

16. A medical component, for use with a second device having a second connector, the medical component comprising:

a first tubular member having a first proximal end and a first distal end;

a first connector affixed to the first proximal end having a plurality of splines and a plurality of slots, where both the plurality of splines and the plurality of slots extend helically along an axial direction to a free end of the first connector, and where each spline in the plurality of splines is spaced apart from an adjacent spline by a slot from the plurality of slots;

wherein the plurality of splines are configured to nest with the second connector and the plurality of slots are configured to receive a portion of the second connector through relative rotation in a first direction between the first connector and the second connector such that, when joined, a joined region the plurality of splines of the first connector and a portion of the second connector each alternatingly form an exterior surface of the joined region, where relative rotation in a second direction allows for uncoupling of the first connector and the second connector; and wherein the plurality of splines of the first connector radially overlap with the plurality of splines of the second connector such that the plurality of splines each have a superior edge and an inferior edge, where increase of a fluid pressure within the medical component forces the inferior edge of an adjacent spline against the superior edge to increase a fluid seal between the plurality of splines.

17. The medical component of claim 16, wherein an end of at least one of the plurality of splines on the first connector comprises a tapered shape.

18. The medical component of claim 16, wherein an angle of the plurality of splines relative to an axis of the first connector is 45 degrees or greater.

19. The medical component of claim 16, further comprising a flow occluding device having at least one flow occluding element, wherein the flow occluding device is advanceable through the first connector and into such that the at least one flow occluding element is positioned within the first tubular member distal to the first connector.

20. The medical component of claim 19, wherein the flow occluding device includes an alignment structure that extends from the first connector when decoupled from the second connector.

21. An adjustable length catheter comprising:
- a first tubular member having a first connector at a proximal end of the first tubular member, where the first tubular member is configured to be advanceable through tortuous vascular paths of a body;
- a second tubular member having a second connector at a distal end of the second tubular member;
- where the first connector and the second connector each have a plurality of splines and a plurality of slots, where both the plurality of splines and the plurality of slots extend helically along an axial direction to a free end of each of the first connector and the second connector;
- wherein the first connector and the second connector are configured to be rotatably coupled into a joined configuration having a joined region, where the plurality of splines and the plurality of slots from the first connector nests respectively with the plurality of slots and the plurality of splines from the second connector such that the plurality of splines of the first connector and the second connector each alternatingly form an exterior surface of the joined region of the first connector and the second connector;
- a sleeve member configured to be removably positioned over at least a portion of the joined region such that the sleeve member increases resistance to relative rotation between the first connector and the second connector; and
- wherein the plurality of splines of the first connector radially overlap with the plurality of splines of the second connector such that the plurality of splines each have a superior edge and an inferior edge, where increase of a fluid pressure within the adjustable length catheter forces the inferior edge of an adjacent spline against the superior edge to increase a fluid seal between the plurality of splines.

* * * * *